US009541543B2

(12) United States Patent
Dweik et al.

(10) Patent No.: US 9,541,543 B2
(45) Date of Patent: Jan. 10, 2017

(54) METHOD FOR DIAGNOSING ACUTE ALCOHOLIC HEPATITIS

(71) Applicant: THE CLEVELAND CLINIC FOUNDATION, Cleveland, OH (US)

(72) Inventors: Raed Dweik, Moreland Hills, OH (US); Ibrahim Hanouneh, Cleveland Hts., OH (US); Nizar Zein, Highland Hts., OH (US); David Grove, Middleburg Hts., OH (US); Frank S. Cikach, Jr., Cleveland Hts., OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 14/595,408

(22) Filed: Jan. 13, 2015

(65) Prior Publication Data
US 2015/0140676 A1    May 21, 2015

Related U.S. Application Data

(63) Continuation-in-part of application No. 14/041,602, filed on Sep. 30, 2013, now Pat. No. 8,932,870.

(60) Provisional application No. 61/707,143, filed on Sep. 28, 2012, provisional application No. 61/798,232, filed on Mar. 15, 2013.

(51) Int. Cl.
*G01N 33/497*   (2006.01)
*G01N 33/48*    (2006.01)
*G01N 33/00*    (2006.01)
*G01N 33/68*    (2006.01)
*G01N 33/576*   (2006.01)

(52) U.S. Cl.
CPC .......... *G01N 33/497* (2013.01); *G01N 33/576* (2013.01); *G01N 33/6893* (2013.01); *G01N 2033/4975* (2013.01); *G01N 2800/085* (2013.01); *Y10T 436/171538* (2015.01); *Y10T 436/173845* (2015.01)

(58) Field of Classification Search
CPC ..................... G01N 2800/085; G01N 2800/08; G01N 2800/00; G01N 2033/4975; G01N 2033/497; G01N 33/497; G01N 33/483; G01N 33/48; G01N 33/00; Y10T 436/171538; Y10T 436/173845; Y10T 436/17
USPC ................................................. 436/111, 106
See application file for complete search history.

(56) References Cited

U.S. PATENT DOCUMENTS

| 7,846,739 B2 | 12/2010 | von Bahr et al. |
| 2008/0009070 A1 | 1/2008 | Lin et al. |
| 2011/0066060 A1 | 3/2011 | von Bahr et al. |
| 2012/0157397 A1 | 6/2012 | Hazen et al. |
| 2013/0011849 A1 | 1/2013 | Henkin |
| 2014/0093970 A1 | 4/2014 | Dweik et al. |

OTHER PUBLICATIONS

Wang Changsong et al, Breath Pentane as a Potential Biomarker for Survival in Hepatic Ischemia and Reperfusion Injury—A Pilot Study, PLOS One, Sep. 2012, vol. 7, Issue 9, e44940, pp. 1-8.*
Van den Velde Sandra et al, GC-MS analysis of breath odor compounds in liver patients, Journal of Chromatography B, 2008, 875, pp. 344-348.*
Ascha et al., "The Incidence and Risk Factors of Hepatocellular Carcinoma in Patients with Nonalcoholic Steatohepatitis", Hepatology, 2010, vol. 51, No. 6, pp. 1972-1978.
Bailey et al., "Acute and Chronic Ethanol Increases Reactive Oxygen Species Generation and Decreases Viability in Fresh, Isolated Rat Hepatocytes", Hepatology, 1998, vol. 28, No. 5, pp. 1318-1326.
Beyoglu et al., "The Metabolomic Window into Hepatobiliary Disease", Journal of Hepatology, 2013, vol. 59, pp. 842-858.
Buszewski et al., "Human Exhaled Air Analytics: Biomarkers of Diseases", Biomedical Chromatography, 2007, vol. 21, pp. 553-566.
Constantinou et al., "Application of Metabonomics on an Experimental Model of Fibrosis and Cirrhosis Induced by Thioacetamide in Rats", Toxicology and Applied Pharmacology, 2007, vol. 218, pp. 11-19.
Gao et al., "Alcoholic Liver Disease: Pathogenesis and New Therapeutic Targets", Gastroenterology, 2011, vol. 141, pp. 1572-1585.
Guarner et al., "Intestinal Bacterial Overgrowth and Bacterial Translocation in Cirrhotic Rats with Ascites" Journal of Hepatology, 1997, vol. 26, pp. 1372-1378.
Hanouneh et al., "A Novel Non-Invasive Breath Test Identifies the Severity of Liver Disease", Gastroenterology, 2011, vol. 106, Supplement 2, pp. S130-S131.
Helman et al., "Natural History and Evaluation of Prednisolone Therapy", Annals of Internal Medicine, 1971, vol. 74, No. 3, pp. 311-321.
Klatt et al., "Evaluation of the C-Methacetin Breath Test for Quantitative Liver Function Testing", Z Gastroenterol, 1997, vol. 35, pp. 609-614.

(Continued)

*Primary Examiner* — Christine T Mui
(74) *Attorney, Agent, or Firm* — Tarolli, Sundheim, Covell & Tummino LLP

(57) ABSTRACT

Various methods for determining whether a subject has alcoholic hepatitis are described. In one aspect, a method for determining whether a subject has alcoholic hepatitis is described. The method includes determining the levels of a trimethylamine in a biological sample obtained from the subject. The level of trimethylamine in the biological sample is compared to the control value, and the subject whose level of trimethylamine exceeds the control value is diagnosed as having alcoholic hepatitis. In another aspect of the present invention a method for assessing a subject as having alcoholic hepatitis (AH) includes determining the level of trimethylamine and the level of pentane in a biological sample obtained from the subject. A TAP score is determined based on the concentration of trimethylamine and the concentration of pentane. The subject is diagnosed as having alcoholic hepatitis if the TAP score exceeds a control value.

28 Claims, 4 Drawing Sheets

(56) References Cited

OTHER PUBLICATIONS

Lang et al., "Isoform Specificity of Trimethylamine N-Oxygenation by Human Flavin-Containing Monooxygenase (FMO) and P450 Enzymes. Selective Catalysis by FM03", Biochemical Pharmacology, 1998, vol. 56, pp. 1005-1012.
Li et al., "Fish Odour Syndrome", Canadian Medical Association Journal, May 17, 2011, vol. 183, No. 8, pp. 929-931.
Lucey et al., "Alcoholic Hepatitis", The New England Journal of Medicine, Jun. 25, 2009, vol. 360, No. 26, pp. 2758-2769.
MacSween et al., "Histologic Spectrum of Alcoholic Liver Disease", Seminars in Liver Disease, 1986, vol. 6, No. 3, pp. 221-232.
Manning et al., "Diagnosis and Quantitation of Fibrosis", Gastroenterology, 2008, vol. 134, pp. 1670-1681.
Mashir et al., "Effect of the Influenza a (H1N1) Live Attenuated Intranasal Vaccine on Nitric Oxide (FENO) and Other Volatiles in Exhaled Breath", Journal of Breath Research, 2011, vol. 5, pp. 1-6.
Meagher et al., "Alcohol-Induced Generation of Lipid Peroxidation Products in Humans", The Journal of Clinical Investigation, 1999, vol. 104, No. 6, pp. 805-813.
Mendenhall et al., "Antibodies to Hepatitis B Virus and Hepatitis C Virus in Alcoholic Hepatitis and Cirrhosis: Their Prevalence and Clinical Relevance", Hepatology, 1991, vol. 14, No. 4., pp. 581-589.
Mitchell et al., "Trimethylamine and Foetor Hepaticus", Scand J. Gastroenterol, 1999, No. 5, pp. 524-528.
Mitchell et al., "Trimethylaminuria: The Fish Malodor Syndrome", Drug Metabolism and Disposition, 2001, vol. 29, No. 4, Part 2, pp. 517-521.
Alvarez et al., "Primary Trimethylaminuria: The Fish Odor System", Servicio de Endocrinologia y Nutricion. Hospital Infanta Elena. Madrid Espana, 2009, vol. 59, No. 6, pp. 337-340. English translation of Abstract included.
O'Shea et al., "Alcoholic Liver Disease", American Journal of Gastroenterology, 2010, vol. 105, pp. 14-32.
Paschke et al., Clinical Applications of Breath Testing, Medicine Reports, 2010, vol. 2, No. 56, pp. 1-6.
Poniachik et al., "The Role of Laparoscopy in the Diagnosis of Cirrhosis", Gastrointestinal Endoscopy, 1996, vol. 43, No. 6, pp. 568-571.
Prince et al., "Application of Selected Ion Flow Tube Mass Spectrometry to Real-Time Atmospheric Monitoring", Rapid Communications in Mass Spectrometry, 2010, vol. 24, pp. 1763-1769.
Rao et al., "Endotoxemia and Gut Barrier Dysfunction in Alcoholic Liver Disease", Hepatology, 2009, vol. 50, No. 2, pp. 638-644.
Riely et al., "Ethane Evolution: A New Index of Lipid Peroxidation", Science, vol. 183, pp. 208-210, 1974.
Ross, "Sub-Parts Per Billion Detection of Trace Volatile Chemicals in Human Breath Using Selected Ion Flow Tube Mass Spectrometry", BMC Research Notes, 2008, vol. 1, No. 41, pp. 1-5.
Smith et al., "Selected Ion Flow Tube Mass Spectrometry (SIFT-MS) for On-Line Trace Gas Analysis", Mass Spectrometry Reviews, 2005, vol. 24, pp. 661-700.
Wang et al., "Gut Flora Metabolism of Phosphatidylcholine Promotes Cardiovascular Disease", Nature, 2011, vol. 472, pp. 57-66.
Wranne, "Urinary Excretion of Trimethylamine and Trimethylamine Oxide", Acta Medica Scandinavica 1956, vol. 153, Issue 6, pp. 433-441.
Yan et al., "Enteric Dysbiosis Associated with a Mouse Model of Alcoholic Liver Disease", Hepatology, 2011, vol. 53, No. 1, pp. 96-105.
Yi et al., "Over Production of Nitric Oxide and Peroxynitrite in Patients with Liver Cirrhosis and Cancer Suppresses Flavin-Containing Monooxygenase (FMO) Activity and Causes Trimethylaminuria (TMAU)", 2001, vol. 15, No. 6, p. A576. Abstract only.
Yoon et al., "Surveillance Report #88. Liver Cirrhosis Mortality in the United States, 1970-2007", National Institute on Alcohol Abuse and Alcoholism Division of Epidemiology and Prevention Research Alcohol Epidemiologic Data System, 2010, pp. 1-24.
Zhang et al., "Dietary Precursors of Trimethylamine in Man: A Pilot Study", Food and Chemical Toxicology, 1999, vol. 37, pp. 515-520.
Zhou et al., "Mutation, Polymorphism and Perspectives for the Future of Human Flavin-Containing Monooxygenase 3", Mutation Research, 2006, pp. 165-171.
PCT International Search Report and Written Opinion for PCT/US2013/062626, mailed Nov. 15, 2013, pp. 1-10.
Hanouneh et al., "The Breathprints in Patients with Liver Disease Identify Novel Breath Biomarkers in Alcoholic Hepatitis", Clinical Gastroenterology and Hepatology, 2014, pp. 1-8.
Cap et al., "Selected ion flow tube mass spectrometry of exhaled breath condensate headspace." Rapid Communications in Mass Spectrometry 22.18 (2008): 2844-2850.
Molina et al., "Design-of-experiment optimization of exhaled breath condensate analysis using a miniature differential mobility spectrometer (DMS)." Analytica Chimica Acta 628.2 (2008): 155-161.
Whittle et al., "Human breath odors and their use in diagnosis." Annals of the New York Academy of Sciences 1098.1 (2007): 252-266.
Moscarella, S., et al. "Expired hydrocarbons in patients with chronic liver disease." Hepato-gastroenterology 31.2 (1984): 60-63.
Mueller, Sebastian, Helmut Karl Seitz, and Vanessa Rausch. "Non-invasive diagnosis of alcoholic liver disease." World J Gastroenterol 20.40 (2014): 14626-41.
PCT International Search Report and Written Opinion for PCT/US2016/012825, mailed Mar. 31, 2016, pp. 1-12.

* cited by examiner

METHOD FOR DIAGNOSING ACUTE ALCOHOLIC HEPATITIS

RELATED APPLICATIONS

This patent application claims priority to application Ser. No. 14/041,602 entitled "Method and Apparatus for Diagnosing Acute Alcoholic Hepatitis" filed on Sep. 30, 2013 which published as U.S. Patent Publication No. 2014/0093970 dated Apr. 3, 2014, which claims priority to Application Ser. No. 61/707,143 entitled "Method and Apparatus for Diagnosing Acute Alcoholic Hepatitis" filed on Sep. 28, 2012 and Application Ser. No. 61/798,232 entitled "Method and Apparatus for Diagnosing Acute Alcoholic Hepatitis" filed on Mar. 15, 2013, all of which are incorporated by reference herein.

TECHNICAL FIELD

The present invention relates generally to methods for diagnosing acute alcoholic hepatitis. More specifically, the present invention relates to methods for diagnosing acute alcoholic hepatitis by determining the level volatile organic compounds in a breath sample from the subject.

BACKGROUND

Alcoholic liver disease is a major cause of chronic liver disease worldwide. The spectrum of alcoholic liver disease includes simple steatosis, fibrosis, cirrhosis, and superimposed hepatocellular carcinoma. In patients with underlying alcoholic liver disease and heavy alcohol intake, episodes of superimposed acute alcoholic hepatitis (AH) may occur. In severe cases, AH leads to severe complications related to liver failure and portal hypertension and has high short-term mortality. Despite the profound economic and health impact of AH, little progress has been made in the management of patients with this severe clinical conditions; and no new drugs for alcoholic hepatitis have been successfully developed since the early 1970s, at which time the use of corticosteroids was proposed for the treatment of severe AH.

In 1951, Soderstrom noted that patients suffering from severe liver disease, when treated with choline, spread an unpleasant odor and that their urine had a very disagreeable smell. A sample of such urine was sent for chemical analysis and TMA was actually isolated. In agreement with this finding, Mitchell et al examined the urine of 63 patients with various liver diseases. In total, 50% of the patients had urinary TMA levels greater than the upper end of the range considered normal (0.08-1.84 microg/ml). Seventeen patients excreted large amounts of free TMA in the urine (>10 microg/ml), above the threshold usually associated with the appearance of a 'fish-like' body odor and tainted breath—traditionally known as fetor hepaticus.

To date, the diagnosis of AH is made clinically based on a typical presentation, with severe liver dysfunction in the context of excessive alcohol consumption, and the exclusion of other causes of acute and chronic liver disease. However, it has been shown that the physician's clinical impression may correlate only moderately well with the diagnosis of AH. Studies that have included a liver biopsy in all patients with clinically diagnosed AH have shown histological confirmation in only 70%-80% of patients. Therefore, in the absence of non-invasive alternatives, liver biopsy remains today the gold standard for the diagnosis of acute AH. However, liver biopsy is an invasive procedure, and it carries a risk of complications. Indeed, 1% to 5% of patients require hospitalization after the procedure. Furthermore, sampling error and interobserver variability add to the limitations of liver biopsy. Therefore, there is an increasing demand for alternative noninvasive methods for the diagnosis of AH.

The clinical use of breath as a medical tool in the diagnosis of chronic liver disease has been reported many years ago in the description of fetor hepaticus "a distinctive musty, sweet breath odor in individuals with severe liver disease". With recent advances in technology, it is possible to identify thousands of substances in the breath, such as volatile compounds and elemental gases. Using selected-ion flow-tube mass spectrometry (SIFT-MS), precise identification of trace gases in the human breath in the parts per trillion ranges can be achieved.

A recent study by Wang et al., (Nature, 2011 Apr. 7; 772(7341): 57-63), has identified a novel pathway linking dietary lipid intake, intestinal microflora and atherosclerosis. Researchers showed that intestinal microflora plays an important role in the formation of trimethylamine (TMA) from dietary phosphatidylcholine and dietary free choline shown in FIG. 1. Hepatic flavin monooxygenase (FMO) family of enzymes, FMO3 convert TMA, a volatile organic compound which smells like rotting fish, into trimethylamine N-oxide (TMAO), an odorless stable oxidation product which contributes to the atherosclerosis in humans. Subjects with chronic liver disease, in general, have impaired capacity to convert TMA into TMAO. Furthermore, alcohol consumption in patients with alcoholic liver disease induces bacterial overgrowth and increases gut permeability and the translocation of bacteria-derived lipopolysaccharides from the gut to the liver. It therefore may be desirable to determine whether the amounts or concentration of volatile compounds in a biological sample, for example, a breath sample correlate with the diagnosis of liver disease.

SUMMARY

In one aspect of the present invention a method is provided for identifying a subject having alcoholic hepatitis (AH) that includes determining the level of trimethylamine (TMA) in a biological sample obtained from the subject using an analytic device; comparing the level of TMA in the biological sample to a control value; and diagnosing a subject as having alcoholic hepatitis if the level of the TMA in the biological sample is elevated as compared to the control value. In one embodiment, the biological sample is an exhaled breath sample.

In another aspect of the present invention, a method of identifying a subject having alcoholic hepatitis (AH) includes determining the level of trimethylamine (TMA) and pentane from the exhaled breath of a subject and determining the level of tremethylamine and pentane in the breath sample and diagnosing the subject as having alcoholic hepatitis if the level of the trimethylamine and pentane in the exhaled breath is elevated compared to the control value.

In another aspect of the present invention, a method of identifying a subject as having alcoholic hepatitis (AH) includes determining the level of trimethylamine (TMA), pentane, and acetone from the exhaled breath of a subject and determining the level of tremethylamine, pentane, and acetone in the breath sample and diagnosing the subject as having alcoholic hepatitis if the level of the trimethylamine, pentane and acetone in the exhaled breath is elevated compared to the control value.

BRIEF DESCRIPTION OF THE FIGURES

The example embodiments of the present invention can be understood with reference to the attached figures. The com

Figure 1:
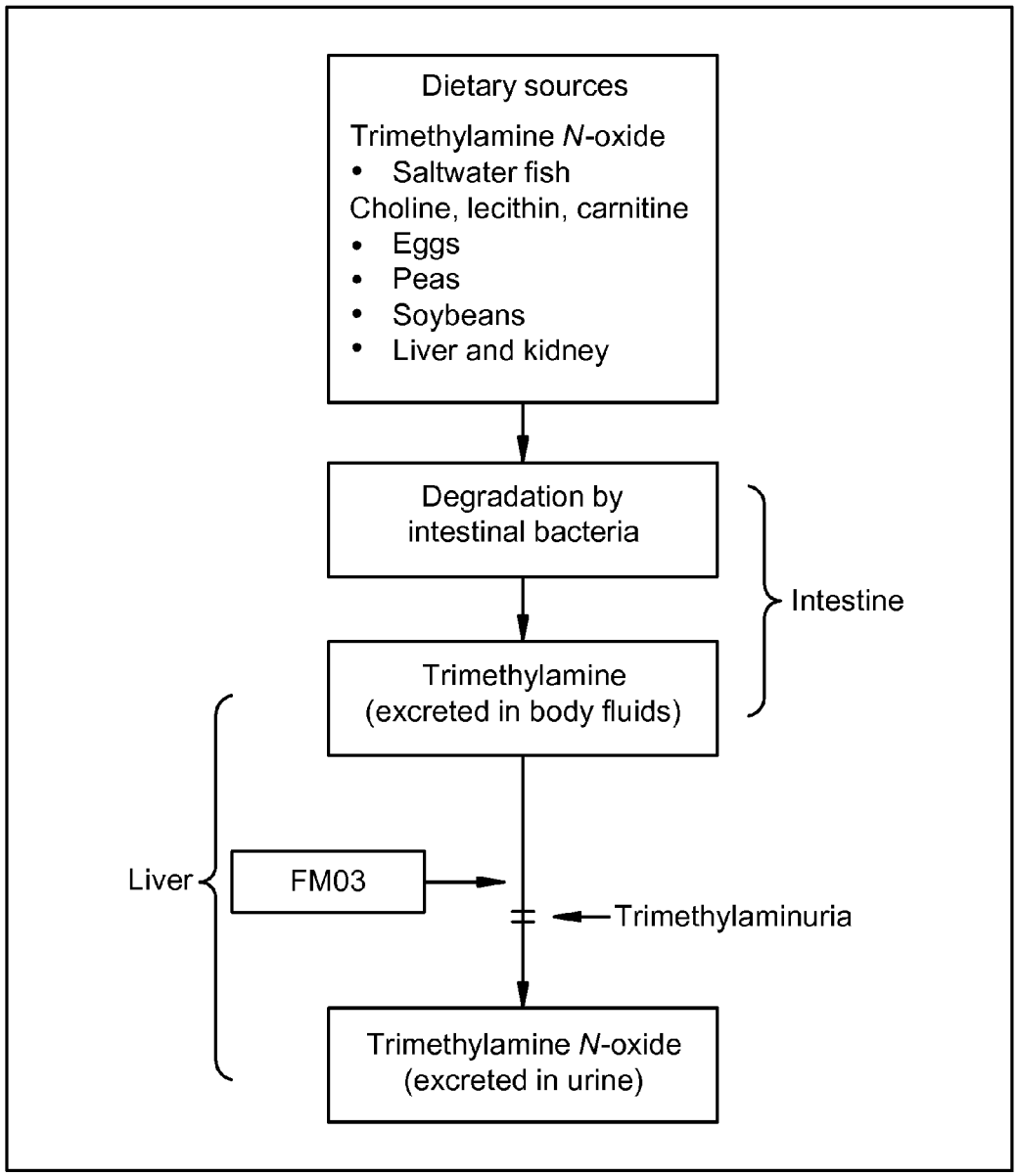
- FIG. 1 is a schematic depiction of the metabolism of dietary Phosphatidylcholine.

In one aspect, the present invention provides a method of identifying a subject having alcoholic hepatitis (AH) that includes determining the level of trimethylamine (TMA) in a biological sample obtained from the subject using an analytic device. The level of TMA in the biological sample is compared to a control value, and the subject is diagnosed as having acute alcoholic hepatitis if the level of the TMA in the biological sample is elevated as compared to the control value. In another embodiment the present invention a method for identifying and determining the amount of substances found in a biological sample of a subject comprises, determining the level of trimethylamine (TMA) in an exhaled breath sample of the subject by an analytical device capable of measuring parts per billion, and comparing the level of trimethylamine in the breath sample to a control value.

DEFINITIONS

As used herein, the term "diagnosis" can encompass determining the existence or nature of disease in a subject. As understood by those skilled in the art, a diagnosis does not indicate that it is certain that a subject certainly has the disease, but rather that it is very likely that the subject has the disease. A diagnosis can be provided with varying levels of certainty, such as indicating that the presence of the disease is 90% likely, 95% likely, or 98% likely, for example. The term diagnosis, as used herein also encompasses determining the severity and probable outcome of disease or episode of disease or prospect of recovery, which is generally referred to as prognosis.

As used herein, the terms "treatment," "treating," and the like, refer to obtaining a desired pharmacologic or physiologic effect. The effect may be therapeutic in terms of a partial or complete cure for a disease or an adverse effect attributable to the disease. "Treatment," as used herein, covers any treatment of a disease in a mammal, particularly in a human, and can include inhibiting the disease or condition, i.e., arresting its development; and relieving the disease, i.e., causing regression of the disease.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. As used herein and in the appended claims, the singular forms "a", "and", and "the" include plural referents unless the context clearly dictates otherwise. Unless otherwise indicated, all numbers expressing quantities used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values; however, inherently contain certain errors necessarily resulting from error found in their respective measurements.

Volatile Organic Compounds

In one aspect of the present invention provides a method of identifying a subject having alcoholic hepatitis that includes determining the level of trimethylamine (TMA) in a biological sample obtained from the subject. Trimethylamine is a volatile organic compound with the formula $N(CH_3)_3$. The term trimethylamine, as used herein, is also intended to encompass salt forms of TMA, such as trimethylamine hydrochloride.

In some embodiments, additional or alternative substrates can be used to diagnose a subject as having alcoholic hepatitis. For example, TMAO is non-volatile compound that can be measured in the blood and urine. Accordingly, in some embodiments, TMAO in the blood and urine could be measured to help determine whether TMAO/TMA ratio can also be used in the diagnosis of acute AH.

Another avenue of diagnosis includes the possibility of the flavin containing monooxygenase 3 (FMO3) enzyme activity being decreased in patients with acute AH compared to patients with other forms of liver disease and healthy control. FMO3 is also known as dimethylaniline monooxygenase, and is encoded by the FMO3 gene. Accordingly, in some embodiments, a method of identifying a subject having acute alcoholic hepatitis is provided that includes determining the level of FMO3 activity in a biological sample obtained from the subject using an analytic device; comparing the level of FMO3 activity in the biological sample to a control value; and diagnosing a subject as having alcoholic hepatitis if the level of the FMO3 in the biological sample is decreased as compared to the control value.

In other aspects of the present invention methods of identifying a subject having alcoholic hepatitis that include determining the level or concentration of at least one of trimethylamine (TMA), pentane and acetone in a biological sample obtained from the subject. Trimethylamine is a volatile organic compound with the formula $N(CH_3)_3$. Pentane is a volatile organic compound with the formula $C_5H_{12}$. Acetone is a volatile organic compound with the formula $(CH_3)_2CO$.

Methods for Determining the Level of Volatile Organic Compounds

With recent advances in technology, it is possible to identify thousands of substances in the breath, such as volatile compounds and elemental gases. Using selected-ion flow-tube mass spectrometry (SIFT-MS), precise identification of trace gases in the human breath in the parts per trillion ranges can be achieved. Using selected-ion flow-tube mass spectrometry, precise identification of TMA in the breath in the parts per billion range (ppb) was achieved on all subjects.

The levels of TMA can be measured by an analytic device, for example, an analytical device that includes an electrochemical sensor, which can be either a portable or a stationary device. The analytic device may be a spectrometric device, such as a mass spectrometer. A spectrometer is a device that uses a spectroscopic technique to assess the concentration or amount of a given species in a medium such as a biological sample (e.g., a bodily fluid). In addition to including equipment used for detecting the level of the risk predictor, the analytic device can also include additional equipment to provide physical separation of analytes prior to analysis (i.e., a separation device). For example, if the analyte detector is a mass spectrometer, it may also include a high performance liquid chromatograph (HPLC) or gas chromatograph (GC) to purify the risk predictor before its detection by mass spectrometry. The separation device and the analyte detector may be provided and referred to as a single device; e.g., HPLC with on-line electrospray ionization tandem mass spectrometry.

In addition to SIFT-MS, the measurement of TMA in the breath can be accomplished using differential mobility spectroscopy (DMS). Differential mobility spectroscopy is a method of detection of quantities of chemicals in air, water, or other fluid that is "on-site". For example, the amount of trimethylamine (TMA) the VOCs herein can be determined by passing a biological sample, such as an exhaled breath sample, into contact with a sensor, for example, an electrochemical sensor.

Biological Samples

"Biological sample" as used herein is meant to include any biological sample from a subject where the sample is suitable for analysis of one or more of the risk factors. Suitable biological samples for determining the level of VOCs, for example TMA, in a subject include but are not limited to bodily fluids such as blood-related samples (e.g., whole blood, serum, plasma, and other blood-derived samples), urine, sputum, cerebral spinal fluid, bronchoalveolar lavage, and the like. Another example of a biological sample is an exhaled breath sample. Risk factor levels can be assessed either quantitatively or qualitatively, usually quantitatively. The levels of the VOCs, for example, TMA, can be determined either in vitro or ex vivo.

The methods involve providing or obtaining a biological sample from the subject, which can be obtained by any known means including needle stick, needle biopsy, swab, and the like. In an exemplary method, the biological sample is a blood sample, which may be obtained for example by venipuncture.

A biological sample may be fresh or stored. Biological samples may be or have been stored or banked under suitable tissue storage conditions. The biological sample may be a bodily fluid or exhaled breath sample expressly obtained for the assays of this invention or a bodily fluid or exhaled breath sample obtained for another purpose which can be subsampled for the assays of this invention. Preferably, biological samples are either chilled after collection if they are being stored to prevent deterioration of the sample.

In some embodiments, the analytical device includes a gas collection component for receiving a biological sample which is a breath sample, and a sensor capable of detecting ppb level of VOC, for example TMA, pentane, acetone, collected in the gas collection component.

Figure 2:
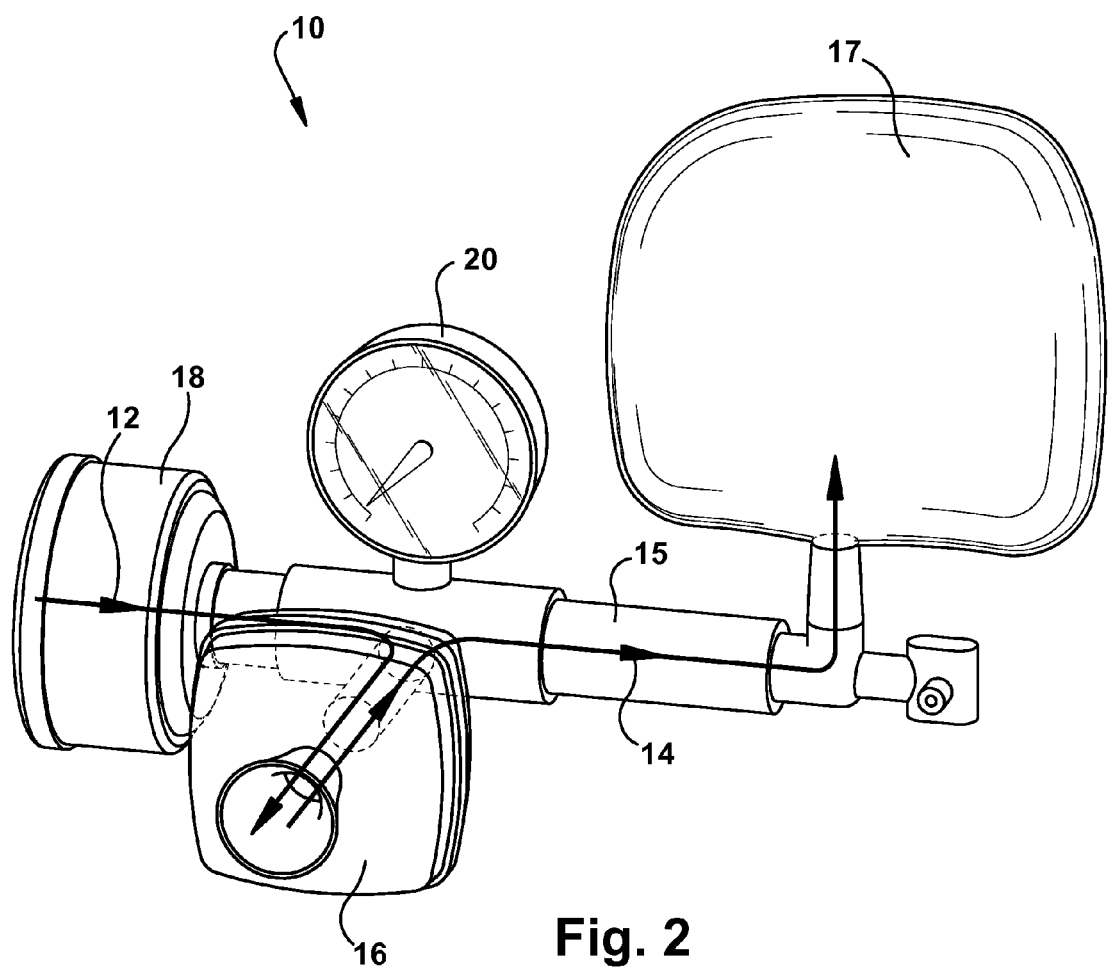
FIG. 2 is a view of an exhaled breath collection device used in the method of determining substances in a biological sample, according to an embodiment of the present invention.

FIG. 2 illustrates an exhaled breath collection device 10, including arrows demonstrating direction of airflow (inhalation as arrow 12 and exhalation as arrow 14) through passageway 15 connected to mouthpiece 16 and used in the method of determining substances in a biological sample, according to examples of the present invention. The breath collection device 10 includes a container 17 for collection of the biological sample, for example the breath sample. The inhaled ambient air of a breath sample can be optionally filtered through an attached filter 18, for example, N7500-2 acid gas cartridge filter, as shown in FIG. 2. The filter 18 can be used to prevent viral and bacterial exposure to the subject and to eliminate exogenous volatile organic compounds from the inhaled air. The exhaled breath sample can be collected into a container 17, such as an attached Mylar® bag, capped, and analyzed. Preferably the breath sample is analyzed as quickly as possible, and should be analyzed within four hours. The exhaled breath collection device 10 optionally includes pressure gauge 20.

Control Values

To determine the likelihood that a subject has AH, the levels of VOCs, for example at least one of TMA, pentane, and acetone, in a biological sample of the test subject are compared to a control value that is derived from levels of TMA in comparable biological samples of control subjects. These control values may have been obtained earlier, in which case they can also be referred to as reference values. In an alternative embodiment, level of VOCs, for example at least one of TMA, pentane, and acetone, in the biological sample of the test subject may then be compared to an internal standard based on levels of other biomolecules in the subject's biological sample. Subjects whose level of VOCs, for example at least one of TMA, pentane, and acetone, is described herein is above the control value or in the higher range of control values or have particular TAP scores in accordance with the aspects of the present invention herein, are diagnosed as having AH. Moreover, the extent of the difference between the subject's VOCs and the control value is also useful for characterizing the likelihood of having AH, and/or the severity of AH, and thereby determining which subjects would most benefit from certain therapies.

Aspects of the present invention also provide a method for monitoring over time the status of AH in a subject who has been diagnosed as having AH. In this context, the method is also useful for monitoring the risk for liver disease progression or regression in a subject with AH. In one example, the method comprises determining the levels of TMA in a biological sample taken from the subject at an initial time and in a corresponding biological sample taken from the subject at a subsequent time. Therefore, an increase in level of TMA in a biological sample taken at the subsequent time as compared to the initial time indicates that the subject's AH has worsened. A decrease in level of TMA indicates that the AH has improved.

In another example, aspects of the present invention provides a method for evaluating therapy in a subject suspected of having or diagnosed as having AH. The method comprises determining level of TMA in a biological sample taken from the subject prior to therapy and determining level of TMA in a corresponding biological sample taken from the subject during or following therapy. A decrease in level of TMA in the sample taken after or during therapy as compared to levels of TMA in the sample taken before therapy is indicative of a positive effect of the therapy on AH in the treated subject.

Subjects

The terms "individual," "subject," and "patient" are used interchangeably herein irrespective of whether the subject has or is currently undergoing any form of treatment. As used herein, the term "subject" generally refers to any vertebrate, including, but not limited to a mammal. Examples of mammals including primates, including simians and humans, equines (e.g., horses), canines (e.g., dogs), felines, various domesticated livestock (e.g., ungulates, such as swine, pigs, goats, sheep, and the like), as well as domesticated pets (e.g., cats, hamsters, mice, and guinea pigs). Treatment of humans is of particular interest.

In any of the examples of the method described herein, the subject may already have liver dysfunction and the diagnosis of acute AH is suspected. In other situations, it is possible that the subject may be healthy.

In certain examples the subject is apparently healthy. "Apparently healthy", as used herein, describes a subject who does not have any signs or symptoms of AH or has not previously been diagnosed as having any signs or symptoms indicating the presence of alcoholism or liver disease.

In other examples, the subject has been diagnosed as having liver disease. Symptoms of liver disease are well known to those skilled in the art, and include symptoms related to liver dysfunction include both physical signs and a variety of symptoms related to digestive problems, blood sugar problems, immune disorders, abnormal absorption of fats, and metabolism problems. Examples of liver disease include hepatitis, alcoholic hepatitis, fatty liver disease, cirrhosis of the liver, liver cancer, biliary cirrhosis, Budd-Chiari syndrome, and Gilbert's syndrome. A number of liver function tests are available to test the proper function of the liver. These test for the presence of enzymes in blood that are normally most abundant in liver tissue, metabolites or products. Liver function tests can evaluate serum proteins, serum albumin, serum globulin, A/G Ratio, alanine transaminase, aspartate transaminase, prothrombin time, partial thromboplastin time, and/or platelet count.

In other examples, the subject has been diagnosed as having alcoholism. Alcoholism includes alcohol abuse and alcohol dependence. Screening for alcoholism is generally conduced using questionnaires designed to detect overuse and loss of control with regard to alcohol consumption. Alcoholism is also defined by the DSM-IV diagnosis of alcohol dependence, which defines alcoholism as the maladaptive alcohol use with clinically significant impairment as manifested by at least three of the following within any one-year period: tolerance; withdrawal; taken in greater amounts or over longer time course than intended; desire or unsuccessful attempts to cut down or control use; great deal of time spent obtaining, using, or recovering from use; social, occupational, or recreational activities given up or reduced; continued use despite knowledge of physical or psychological sequelae.

Alcoholic Hepatitis

Chronic consumption of alcohol results in the secretion of pro-inflammatory cytokines (TNα-, IL6 and IL8), oxidative stress, lipid peroxidation, and acetaldehyde toxicity. These factors cause inflammation, apoptosis and eventually fibrosis of liver cells. The spectrum of alcoholic liver disease includes simple steatosis (fatty liver), fibrosis, and cirrhosis. Fatty change, or steatosis is the accumulation of fatty acids in liver cells. These can be seen as fatty globules under the microscope. Alcoholism causes development of large fatty globules (macro vesicular steatosis) throughout the liver and can begin to occur after a few days of heavy drinking. Alcoholic hepatitis is characterized by the inflammation of hepatocytes. Cirrhosis is a late stage of serious liver disease marked by inflammation (swelling), fibrosis (cellular hardening) and damaged membranes preventing detoxification of chemicals in the body, ending in scarring and necrosis (cell death). A variety of tests are available to assess alcoholic liver damage. Besides blood examination, ultrasound and a CT scan can also be used to assess liver damage. In addition, a liver biopsy can be performed.

In patients with underlying alcoholic liver disease and heavy alcohol intake, episodes of superimposed acute AH may occur. Acute AH, as used herein, refers to alcoholic hepatitis that has progressed to the liver cirrhosis stage.

Therapeutic Intervention

Aspects of the present invention also relates to methods of identifying a subject in need of alcoholic hepatitis therapeutic intervention. The therapeutic intervention can be surgery, administration of a therapeutic agent, or implementation of a beneficial life style change by the subject. In one example, the method comprises recommending administration or administering to the subject identified as having alcoholic hepatitis a suitable pharmacological agent. In another example, the method includes recommendation of and/or implementation of a beneficial life style change by the subject.

Beneficial lifestyle changes include cessation of alcohol consumption. This is the only way to reverse liver damage or prevent liver injury from worsening. Another beneficial lifestyle change is improved nutrition. A calorie-rich diet is recommended to help the liver in its regeneration process. Dietary fat must be reduced because fat interferes with alcohol metabolism. The diet is usually supplemented with vitamins and dietary minerals (including calcium and iron). Many nutritionists recommend a diet high in protein, with frequent small meals eaten during the day, about 5-6 instead of the usual 3. Nutritionally, supporting the liver and supplementing with nutrients that enhance liver function is recommended. These include carnitine, which will help reverse fatty livers, and vitamin C, which is an antioxidant, aids in collagen synthesis, and increases the production of neurotransmitters such as norepinephrine and serotonin, as well as supplementing with the nutrients that have been depleted due to the alcohol consumption.

Subjects having "acute AH" have a 50% or greater chance of death within 30 days. Short term treatment may include hospitalization or specific therapies for suppressing inflammation of the liver and improved functioning of the liver.

In some examples, therapeutic intervention includes administration of a pharmaceutical agent. Examples of pharmaceutical agents known to be useful for treating AH include corticosteroids for severe cases, anticytokines (infliximab and pentoxifylline), propylthiouracil to modify metabolism and colchicine to inhibit hepatic fibrosis.

In further examples, the therapeutic intervention is surgery. The main surgical option, which is generally used as a last resort, is a liver transplant. One of the criteria to become eligible for a liver transplant is to discontinue alcohol consumption for a minimum of six months.

In another example, the present invention relates to kits that include reagents for assessing the level of at least one of TMA in biological samples obtained from a test subject. In certain examples, the kits also include printed materials such as instructions for practicing the present methods, or information useful for assessing a test subject's risk of having AH. Examples of such information include, but are not limited to cut-off values, sensitivities at particular cut-off values, as well as other printed material for characterizing risk based upon the outcome of the assay. In some examples, such kits may also comprise control reagents, e.g. known amounts of TMA or other VOCs.

VOC Levels

As described herein, patients with AH can be shown to have higher levels of at least one of TMA, pentane, and acetone in the exhaled breath compared to patients with other forms with liver disease and to healthy controls. It has been found herein that the level of trimethylamine (TMA) from a biological sample of a subject that is equal to or exceeds a control value or cutoff value of 14 ppb, in another example a value of 21 ppb and in another example a value of 31 ppb can be diagnosed with alcoholic hepatitis. For example, the results below have found that using a cutoff value or control value of breath TMA of 31 ppb may provide around 94% specificity and 98% sensitivity for the diagnosis of acute AH. The lower levels of TMA can provide good sensitivity and therefore provide a good screening as to whether a patient does not have AH if the level is below the cutoff value. High ppb values may indicate high specificity and a high probability that the patient has AH. Accordingly, it is found herein that the exhaled breath as a suitable alternative or compliment to standard clinical methods in assessing the diagnosis of AH. In one embodiment of the present invention, the method for identifying amounts of substances in a biological sample includes determining the level of trimethylamine (TMA) in a biological sample obtained from a subject and comparing it to a control value to determine whether the subject has alcoholic hepatitis (AH). A biological sample having level of the trimethylamine (TMA) in the biological sample that is elevated as compared to the control value has alcoholic hepatitis.

Accordingly, TMA cutoff range or control value may depend on the standard of specificity and sensitivity, which may vary. Accordingly, in one aspect of the present invention, a method for determining AH has a cutoff value of about 14 ppb trimethylamine (TMA), in another example the level of TMA is at least about 21 ppb, in another example the cutoff value ranges from about 20 ppb TMA to about 40 ppb TMA, in another example a TMA level that ranges from about 25 ppb TMA to about 35 ppb TMA, in another example, from about 28 ppb TMA to about 32 ppb TMA, and in yet another example, the cutoff value ranges from about 30 ppb to about 35 ppb.

In other aspects of the present invention, a method for assessing a subject as having acute alcoholic hepatitis (AH) comprising: receiving an exhaled breath sample from a subject; determining the level of trimethylamine (TMA) and the level of pentane in the exhaled breath sample obtained from the subject using an analytical device; determining a TAP score based on the concentration of trimethylamine and pentane in the exhaled breath; and diagnosing the subject as having alcoholic hepatitis based on the TAP score exceeding a control value. The TAP score utilizing TMA and pentane concentrations is determined according to the formula:

$$TAP\ score = 100 \times (exp[lr]/1 + exp[lr]),\ wherein$$

$$(lr = -3.71 + [0.34 \times TMA] - [0.087 \times pentane]).$$

In another example, a subject is diagnosed as having alcoholic hepatitis when the TAP score is at least about 30, in another example at least about 34, and in another example at least about 36. In another example, the subject is diagnosed as having alcoholic hepatitis when the TAP score ranges from about 36 to about 67, and yet in another example, the subject is diagnosed as having alcoholic hepatitis when the TAP score is at least about 67 or greater. The lower TAP scores can provide good sensitivity and therefore provide a good screening as to whether a patient does not have AH if the level is below the cutoff value, and thus can be used to rule out the disease. High ppb values may indicate high specificity and a high probability that the patient has AH with a high degree of confidence.

In another aspect of the present invention a method for assessing a subject as having acute alcoholic hepatitis (AH) comprising: receiving an exhaled breath sample from a subject; determining the level of trimethylamine (TMA), the level of acetone and the level of pentane in the exhaled breath sample obtained from the subject using an analytical device; determining a TAP score based on the concentration of trimethylamine, acetone and pentane in the exhaled breath; and diagnosing the subject as having alcoholic hepatitis determining a TAP score based on the concentration of trimethylamine and pentane in the exhaled breath; and diagnosing the subject as having alcoholic hepatitis bases on the TAP score exceeding a control value.

The TAP score utilizing TMA, acetone, and pentane concentrations is determined according to the formula:

$$TAP\ score = 100 \times (exp[lr]/1 + exp[lr]),\ wherein$$

$$(lr = -4.39 + [0.46 \times trimethylamine] - [0.0032 \times acetone] - (0.091 \times pentane)].$$

In another example, a subject is diagnosed as having alcoholic hepatitis when the TAP score is at least about 20, in another example at least about 25, and in another example at least about 28. In another example, the subject is diagnosed as having alcoholic hepatitis when the TAP score ranges from about 25 ppb to about 55 ppb, in another example from about 28 ppb to about 51 ppb. In another example the TAP score is at least about 51.

In another aspect a method of identifying a subject having acute alcoholic hepatitis (AH), comprising: receiving an exhaled breath sample from a subject; determining the level of pentane in the exhaled breath sample obtained from the subject using an analytic device; and diagnosing a subject as having alcoholic hepatitis if the exhaled breath sample contains a level of pentane that is at least about 50 ppb. In another example, a subject as having alcoholic hepatitis if the exhaled breath sample contains a level of pentane that is at ranges from about 40 ppb to about 50 ppb.

In another aspect a method of identifying a subject having acute alcoholic hepatitis (AH), comprising: receiving an exhaled breath sample from a subject; determining the level of acetone in the exhaled breath sample obtained from the subject using an analytic device; and diagnosing a subject as having alcoholic hepatitis if the exhaled breath sample contains a level of acetone that is at least about 440 ppb. In another example, a subject as having alcoholic hepatitis if the exhaled breath sample contains a level of acetone that is at ranges from about 450 ppb to about 550 ppb.

In any of the examples described above, a method for identifying a subject having acute alcoholic hepatitis (AH), optionally includes rinsing the mouth of the subject prior to receiving the exhaled breath sample. In other examples, the method for identifying a subject having acute alcoholic hepatitis (AH), optionally includes the step of the subject inhaling and exhaling a breath before inhaling and exhaling for the breath collection.

Examples have been included to more clearly describe a particular example of the invention and its associated cost and operational advantages. However, there are a wide variety of other embodiments within the scope of the present invention, which should not be limited to the particular example provided herein.

Examples

It's known from prior studies that TMA is metabolized by the liver to form TMAO. It remained unknown, however, that why only a subgroup of patients with liver disease excretes large amount of TMA. According to study data, a subgroup of patients with acute AH have significantly higher levels of at least one of TMA, pentane and acetone compared to patients with other forms with liver disease and to healthy controls.

Studies were conducted of human subjects that included patients with various liver diseases and also healthy subjects to determine whether elevated levels of compounds identified in biological samples of breath contributed to chronic liver disease, and whether elevated levels of compounds correlate with the diagnosis of alcoholic hepatitis (AH).

Patients with liver disease attending the gastroenterology outpatient and inpatient facilities at the Cleveland Clinic were prospectively recruited. The study population was divided into four groups: acute AH, acute non-alcoholic hepatitis, chronic alcoholic liver disease, and chronic non-alcoholic liver disease. Two control groups without liver disease were identified: healthy alcoholic and healthy non-alcoholic volunteers.

The diagnosis of acute AH was made based on the presence of the following laboratory criteria in a patient with ascites and a history of heavy alcohol use (16): 1) aspartate aminotransferase level that is elevated, but <300 IU per milliliter; 2) ratio of aspartate aminotransferase level to the alanine aminotransferase level that is more than 2; 3) total serum bilirubin level of more than 5 mg per deciliter; 4) an elevated INR, and 5) neutrophilia. Liver biopsy was considered when the diagnosis of acute AH was uncertain. Confirmatory microscopic findings of acute AH include steatosis and hepatocellular injury characterized by ballooned hepatocytes that contain amorphous eosinophilic inclusion bodies called Mallory bodies, and surrounded by neutrophils. Additionally, the presence of Intrasinusoidal fibrosis is a characteristic lesion of alcoholic hepatitis.

"Significant alcohol intake" was defined as a consumption of more than two drinks daily or more than six drinks daily on weekends for the past 5 years. Other causes of liver disease in patients with significant alcohol intake have been excluded. These include chronic viral hepatitis, drug-induced liver injury, Wilson's disease, autoimmune liver disease, alpha-1 antitrypsin deficiency, and decompensation associated with hepatocellular carcinoma.

Those individuals with ongoing tobacco use were excluded from the study. Additionally, patients with liver cancer or other malignancies were excluded as well as those with prior history of transplantation.

SIFT-MS breath analysis was performed on all subjects to measure TMA in the exhaled breath as described below. Breath samples were collected in the fasting state upon admission in patients with acute hepatitis and during office visits in other research groups. Furthermore, blood samples were obtained at the time of the breath test and used to measure complete blood count, basic metabolic panel and liver function tests. The Model of End-Stage Liver Disease (MELD) score and Child's Pugh classification and score were calculated as well.

Age, gender, ethnicity, and the etiology of underlying liver disease were recorded for each subject. Furthermore, the electronic medical record was reviewed for laboratory and diagnostic investigations including complete blood counts, basic metabolic panel, liver function tests, ultrasound studies, as well other imaging studies when available.

Exhaled Breath Collection

All subjects completed a mouth rinse with water prior to the collection of the breath sample in order to reduce the contamination from volatile organic compounds (VOCs) produced in the mouth. Subjects were prompted to exhale normally to release residual air from the lungs and then inhale to lung capacity through a disposable mouth filter (FIG. 2). The inhaled ambient air was also filtered through an attached N7500-2 acid gas cartridge. The filters were used to prevent viral and bacterial exposure to the subject and to eliminate exogenous VOCs from the inhaled air. The subjects then proceeded to exhale at a rate of 350 ml/s through the mouth filter until the lungs were emptied. The exhaled breath sample was collected into an attached Mylar® bag, capped, and analyzed within four hours. Mylar® bags were cleaned by flushing with nitrogen between subjects.

Selected-Ion Flow-Tube Mass Spectrometry (SIFT-MS)

The exhaled breath samples underwent gas analysis using SIFT-MS on a VOICE200® SIFT-MS instrument (Syft Technologies Ltd, Christchurch, New Zealand). The SIFT-MS technology and instrument used in this study have been described in the prior art.

Patients with liver disease were prospectively recruited from a single tertiary care center. The study population was divided into four groups: acute AH (N=17), acute non-alcoholic hepatitis (N=21), chronic alcoholic liver disease (N=29), and chronic non-alcoholic liver disease (N=42). Two control groups without liver disease were identified: healthy alcoholic (N=8) and healthy non-alcoholic volunteers (N=16). Using selected-ion flow-tube mass spectrometry, precise identification of TMA in the breath in the parts per billion range (ppb) was achieved on all subjects. Breath samples were collected in the fasting state upon admission in patients with acute hepatitis and during office visits in other research groups. One hundred thirty-three (133) subjects were included in the study, of whom 17 had AH. The mean MELD score and Maddrey's Discriminant Function in patients with AH were 26.1±8.0 and 51.1±27.1 respectively. Subjects with AH were followed over 2.0±2.1 months during which 6/17 (35%) died. The mean concentration of TMA in the exhaled breath was remarkably higher in patients with AH compared to patients with other forms of liver disease and to healthy volunteers (p<0.001). With exception of AH, the levels of breath TMA were not different between patients with various forms of liver disease and healthy volunteers (p>0.05). With the use of ROC curve, a cutoff value of breath TMA of 31 ppb provides 94% specificity and 98% sensitivity for the diagnosis of AH [AUC 95% CI: 0.990 (0.977-1)]. Among patients with AH, the concentration of TMA in the exhaled breath moderately correlates with the MELD score [rho (95% CI): 0.53 (0.04, 1.0); p=0.035], but not with Maddrey's Discriminant Function (rho=0.36, p=0.17). The levels of breath TMA were not associated with survival rates in patients with AH (p=0.50).

Mass scans of the products ions generated in the chemical ionization mass spectrum for each reagent ion ($H_3O^+$, $NO^+$, and $O_2^+$) were obtained in the mass scanning (MS) mode. MS between 14-200 amu was used to identify significant peaks at product ion masses representing unknown breath volatiles relating to liver cirrhosis. More accurate concentration data was obtained by selected ion monitoring (SIM) of product ions of fourteen pre-selected compounds: 2-propanol, acetaldehyde, acetone, acrylonitrile, ammonia, benzene, carbon disulfide, dimethyl sulfide, ethanol, hydrogen sulfide, isoprene, pentane, triethylamine, and trimethylamine. These compounds have been previously identified as common constituents of exhaled breath in patients with and without liver cirrhosis. The fourteen pre-selected compounds for SIM analysis were monitored using the product ions listed in Table 1.

The MS data was normalized to account for variability in the precursor ion intensity by dividing each mass signal by the sum of the corresponding precursor ion signals. Normalization was not required for the SIM data because absolute concentrations of SIM analytes were calculated from the precursor ion to product ion count ratios by the built-in LabSyft software and libraries (Syft Technologies Ltd., Christchurch, New Zealand).

TABLE 1

Product ions of 14 compounds used in SIM

| Analyte | Precursor | Mass |
|---|---|---|
| 2-propanol | $H_3O^+$ | 43 [15] |
|  | $H_3O^+$ | 61 |
|  | $NO^+$ | 59 |
| Acetaldehyde | $NO^+$ | 43 [16] |
|  | $O_2^+$ | 44 |
| Acetone | $NO^+$ | 88 [16] |
| Acrylonitrile | $H_3O^+$ | 54 [17] |
|  | $NO^+$ | 53 |
| Ammonia | $O_2^+$ | 17 [18] |
| Benzene | $NO^+$ | 108 [19] |
|  | $O_2^+$ | 78 |
| Carbon disulfide | $O_2^+$ | 76 [20] |
| Dimethyl sulfide | $NO^+$ | 62 [20] |
|  | $O2+$ | 62 |
| Ethanol | $H_3O^+$ | 47 [15] |
|  | $NO^+$ | 45 |
| Hydrogen sulfide | $H_3O^+$ | 35 |
| Isoprene | $O_2^+$ | 67 [19] |
| Pentane | $O_2^+$ | 42 [19] |
| Triethylamine | $H_3O^+$ | 102 [20] |
|  | $NO^+$ | 101 |
| Trimethylamine | $H_3O^+$ | 58 [18] |
|  | $H_3O^+$ | 60 |

Statistical Analysis

Descriptive statistics were computed for all variables. These include means, standard deviations and percentiles for continuous factors and frequencies and percentages for categorical variables. Univariable analysis was performed to compare the groups. Analysis of Variance (ANOVA) or the non-parametric Kruskal-Wallis test were used to compare continuous factors and Pearson's chi-square tests were used for categorical variables; post-hoc pair-wise comparisons were done using a significance criterion of 0.005 (0.05/10) in order to account for multiple comparisons. Analysis of Covariance (ANCOVA) was performed to assess differences in TMA levels between disease groups after adjusting for age and gender; the inverse of the third root of TMA ($(TMA)^{-1/3}$) was modeled as the dependent variable with group, age and gender as the independent variables.

In addition, subgroup analyses were carried out to study associations between TMA and clinical factors in the different liver disease groups. Spearman's correlation coefficients were used to evaluate correlation between TMA and variables such as MELD, Child Pugh Score, bilirubin, INR, creatinine and Maddrey's Discriminant Function. Wilcoxon rank sum tests were used to study associations between TMA and categorical factors such as presence of ascites, encephalopathy, varices. Cox regression was used to study the effect of TMA levels on mortality of subjects with acute alcoholic hepatitis; the hazard ratio and corresponding 95% confidence interval are reported. A p<0.05 was considered statistically significant. All analyses were performed using SAS (version 9.2, The SAS Institute, Cary, N.C.) and R (version 2.13.1, The R Foundation for Statistical Computing, Vienna, Austria).

A total of 133 patients were included in the study, of whom 17 subjects had acute AH, and 21 had acute non-alcoholic hepatitis. The causes of acute non-alcoholic hepatitis included: drug induced (n=12), viral hepatitis (n=5), and autoimmune hepatitis (n=4). Seventy one patients with chronic liver disease met the inclusion criteria of the study; 29 of them were alcoholic while 42 had chronic liver disease secondary to other etiologies [non-alcoholic steatohepatitis (n=19), chronic hepatitis C (n=17), chronic hepatitis B (n=2), alpha-1 antitrypsin deficiency (n=2), primary biliary cirrhosis (n=1) and cardiac cirrhosis (n=1)]. Two control groups without liver disease were identified: healthy alcoholic (n=8) and healthy non-alcoholic volunteers (n=16).

The mean age of the enrolled liver patients was 58±11 years, of whom 18 (65%) were males and 25 (90%) were Caucasians. The mean age of the enrolled healthy control subjects was 34±9, of whom 8 (28.6) were males, and 10 (35.7) were Caucasians. The baseline characteristics of the present study population are shown in Table 2.

TABLE 2

Patients Characteristics

| Factor | Healthy Controls Alcoholic & Non-Alcoholic (N = 24) | Chronic Alcoholic Liver Disease (N = 29) | Chronic Non-Alcoholic Liver Disease (N = 42) | Acute Alcoholic Hepatitis (N = 17) | Acute Non-Alcoholic Hepatitis (N = 21) | p-value |
|---|---|---|---|---|---|---|
| Age | 37.8 ± 13.8 [2] | 58.4 ± 9.7 [145] | 49.0 ± 12.5 | 45.7 ± 12.1 [2] | 44.1 ± 15.3 [2] | <0.001 |
| Male | 6(37.5) | 18(58.1) | 13(76.5) [5] | 8(57.1) | 2(18.2) [3] | 0.026 |
| Ethnicity |  |  |  |  |  | 0.53 |
| Caucasian | 15(93.8) | 25(80.6) | 10(83.3) | 13(92.9) | 11(100.0) |  |
| African-American | 0(0.0) | 5(16.1) | 1(8.3) | 1(7.1) | 0(0.0) |  |
| Asian | 1(6.3) | 1(3.2) | 1(8.3) | 0(0.0) | 0(0.0) |  |
| TMA (ppb) | 6.6 [5.5, 9.3] [34] | 13.3 [6.7, 18.0] [4] | 12.1 [10.5, 14.3] [14] | 55.7 [33.6, 97.0] [1235] | 4.9 [2.6, 14.7] [4] | <0.001 |

Values presented as Mean ± SD with ANOVA; Median [P25, P75] with Kruskal-Wallis test, or N (%) with Pearson's chi-square test.
[1] Significantly different from Healthy Controls
[2] Significantly different from chronic alcoholic liver disease
[3] Significantly different from chronic non-alcoholic liver disease
[4] Significantly different from Acute Alcoholic Hepatitis
[5] Significantly different from Acute non-alcoholic hepatitis
A significance level of 0.005 was used for pairwise ad-hoc comparisons.

Among patients with chronic liver disease (alcoholic and non-alcoholic), 31 subjects had liver cirrhosis. At the time of enrollment, the Child Pugh score of patients with liver cirrhosis was 8.5±2.6, with 11 subjects classified as a class C, 14 patients as a class B, and 7 patients as class A Childs-Pugh-Turcotte. The baseline MELD score in cirrhotic patients was 14.5±7.4. Hepatic encephalopathy was present in 18 patients, of whom seven experienced severe and recurrent encephalopathy that required lactulose and rifaximin combination therapy, while eleven patients had mild encephalopathy controlled with lactulose alone. The prevalence of ascites in the study group was 22 (78%), with the majority 18 (64%) had large ascites that required frequent large volume paracentesis.

Among patients with AH, liver biopsy was necessary to confirm the diagnosis in patients. The mean MELD score and Maddrey's Discriminant Function in patients with AH at the time of presentation were 26.1±8.0 and 51.1±27.1 respectively. Specific therapy for acute AH was used in 11 patients with AH; pentoxifylline was used in nine patients, while steroid was used in 2 subjects.

The Exhaled Breath Analysis in Patients with Liver Disease

Of the 561 product ion masses scanned for in the MS mode, six exhaled breath compounds were identified as being elevated in patients with liver disease compared to healthy controls (Table-3). Those compounds include: 2-propanol, acetaldehyde, ammonia, ethanol, pentane and trimethylamine. Hydrogen sulfide was slightly decreased in patients with liver disease compared to healthy control. There was no difference in the levels of breath acetone, acrylonitrile, benzene, carbon disulfide, isoprene, or triethylamine in patients with liver disease compared to healthy control.

TABLE 3

The exhaled breath analysis in liver disease and healthy control.

| Breath Compound | Liver Patients | Healthy control | P value |
|---|---|---|---|
| 2-propanol | 93 ± 12 | 36 ± 3 | <0.001 |
| Acetaldehyde | 70 ± 6 | 52 ± 8 | 0.004 |
| Ammonia | 100 ± 11 | 78 ± 9 | <0.001 |
| Ethanol | 333 ± 66 | 121 ± 17 | <0.001 |
| Pentane | 38 ± 11 | 20 ± 1 | 0.02 |
| Trimethylamine | 13.9 [7.7, 26.0] | 6.6 [5.5, 9.3] | 0.004 |
| Hydrogen sulfide | 0.3 ± 0 | 0.6 ± 0 | <0.001 |

The Exhaled Breath TMA in Patients with Liver Disease

The level of exhaled breath TMA was significantly higher in patients with liver disease compared to healthy controls. The association between the levels of TMA in the exhaled breath and liver disease remained significant after adjusting for age and gender (Median (95% CI): 12.4 (10, 15.7) vs. 7.0 (4.8, 11.1); p=0.032), as shown in Table-4.

TABLE 4

The levels of exhaled breath TMA in patients with liver disease compared to healthy control.

| Factor | Healthy Control (N = 24) | Liver Disease (N = 109) | p-value |
|---|---|---|---|
| Age | 37.8 ± 13.8 | 51.6 ± 13.0 | <0.001 |
| Male | 6 (37.5) | 41 (56.2) | 0.18 |
| Caucasian | 15 (93.8) | 59 (86.8) | 0.44 |
| Ethnicity | | | 0.35 |

TABLE 4-continued

The levels of exhaled breath TMA in patients with liver disease compared to healthy control.

| Factor | Healthy Control (N = 24) | Liver Disease (N = 109) | p-value |
|---|---|---|---|
| Caucasian | 15 (93.8) | 59 (86.8) | |
| African-American | 0 (0.0) | 7 (10.3) | |
| Asian | 1 (6.3) | 2 (2.9) | |
| TMA (ppb) | 6.6 [5.5, 9.3] | 13.9 [7.7, 26.0] | 0.004 |

Values presented as Mean ± SD with ANOVA;
Median [P25, P75] with Wilcoxon rank sum test, or N (%) with Pearson's chi-square test.

Figure 3:
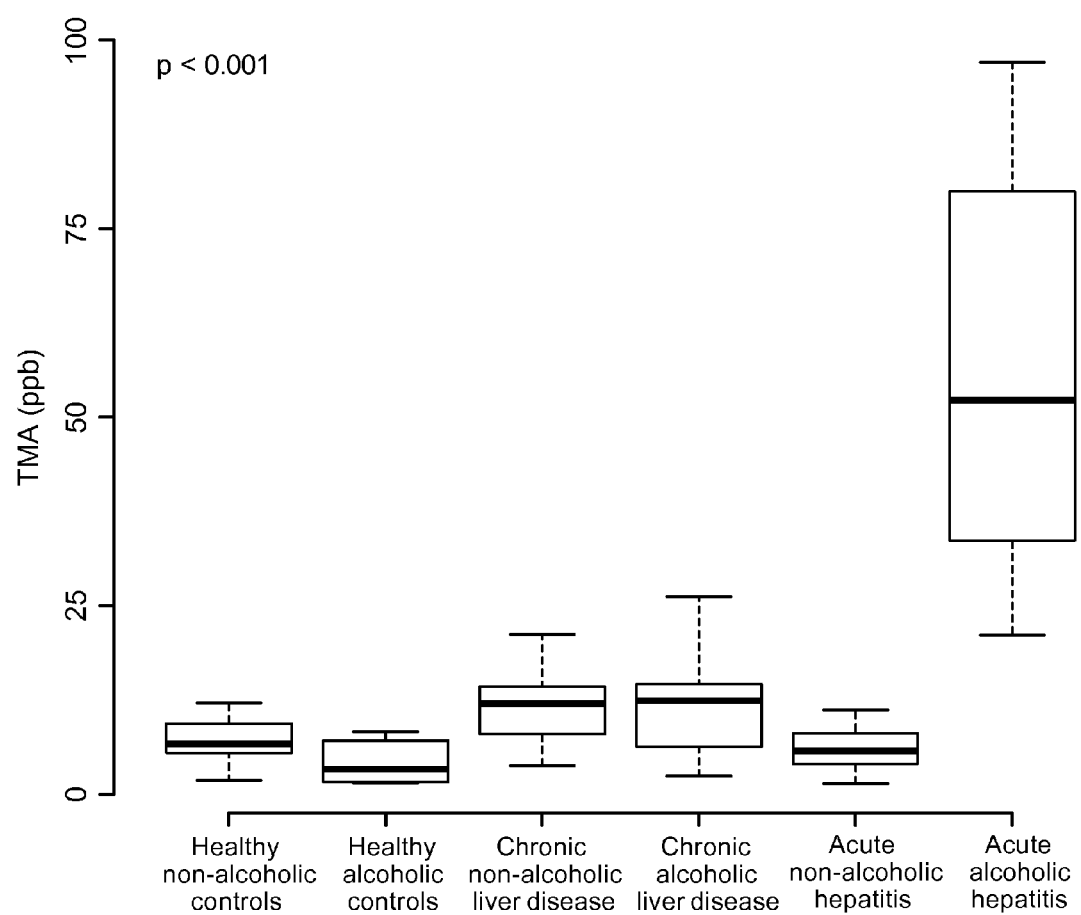
FIG. 3 is a chart depicting Trimethylamine (TMA) levels in the exhaled breath of patients with various forms of liver disease, according to an embodiment of the present invention.

However, with exception of AH, the levels of breath TMA were not different between patients with various forms of liver disease and healthy volunteers (p>0.05), as shown in FIG. 3. The mean concentration of TMA in the exhaled breath was remarkably higher in patients with AH compared to patients with other forms of liver disease and to healthy volunteers (p<0.001), as shown in FIG. 3. After adjusting for age and gender, subjects with acute AH are still shown to have higher TMA levels in the exhaled breath compared to each of the other research groups (p<0.001), as shown in Table-5. With the use of ROC curve, a cutoff value of breath TMA of 31 ppb provides 94% specificity and 98% sensitivity for the diagnosis of acute AH [AUC 95% CI: 0.990 (0.977-1)].

TABLE 5

Age and Gender Adjusted TMA Means: Analysis of Covariance.

| Group | Mean TMA (95% CL) | p-value |
|---|---|---|
| Healthy Controls | 7.1 (5.2, 10.0)[4] | <0.001 |
| Cirrhosis | 10.3 (7.9, 13.6)[45] | |
| Fibrosis | 11.8 (8.4, 17.3)[45] | |
| Acute Alcoholic Hepatitis | 61.8 (34.0, 130.6)[1235] | |
| Acute Hepatitis (no EtOH) | 5.2 (3.8, 7.5)[234] | |

[1]Significantly different from Healthy Controls
[2]Significantly different from Cirrhosis
[3]Significantly different from Fibrosis
[4]Significantly different from Acute Alcoholic Hepatitis
[5]Significantly different from Acute Hepatitis (no EtOH)

The Factors Associated with the Breath TMA in Patients with Liver Disease:

The concentration of exhaled breath TMA in patients with AH moderately correlates with the serum creatinine [rho (95% CI): 0.56 (0.03, 1.0); p=0.039], and with the MELD score [rho (95% CI): 0.53 (0.04, 1.0); p=0.035]. However, there was no significant correlation between the exhaled breath TMA and serum bilirubin (rho=0.11, p=0.16) or the Maddrey's Discriminant Function (rho=0.36, p=0.17). Subjects with AH were followed over 2.2±2.2 months (min, max: 0.13, 7.6 months) during which 6/17 (35%) died. The levels of breath TMA were not associated with survival rates in patients with AH [HR (95% CI): 1.00 (0.99, 1.01), p=0.50].

Among patients with liver cirrhosis, the levels of exhaled breath TMA were not found to be correlated to either Child Pugh score (rho=0.21) or MELD score (rho=0.14). In addition, TMA levels were not associated with the Child Pugh classification [A: 6.7 (5.7, 18.5) vs. B: 13.3 (8.8, 14.5) vs. C: 14.2 (10.2, 24.6); p=0.39]. There were no differences in the levels of exhaled breath TMA between cirrhotic patients with and those without ascites [median (P25, P75): 14.1 (12.5, 18) vs. 8.8 (5.9, 17.8); p=0.19]. Similarly, TMA levels were not different between cirrhotic patients with and those without hepatic encephalopathy [13.3 (8.8, 18) vs. 12.0 (6.2, 17.3); p=0.63].

Among patients with chronic liver disease (alcoholic and non-alcoholic) who underwent a liver biopsy (n=17), 53% of subjects had stage 2 fibrosis on liver biopsy; and the remaining 47% had stage 1 fibrosis. There was no significant association between the stage of fibrosis on liver biopsy and the levels of exhaled breath TMA (stage 1: 11.9 [10.9, 13.7] vs. stage 2: 12.8 [7.7, 19.6]; =0.92).

While previous studies have examined liver disorders, such as alcoholic hepatitis (AH), many of them are invasive and are not commonly used or available in the clinical practice settings.

The observation of elevated levels of TMA in patients with acute AH may suggest that in acute AH, the transformation of TMA to TMAO might be impaired as a consequence of a damaged liver function. This theory is based on the recognition of the etiology of an uncommon genetic disorder called trimethylaminuria, also known as fish malodour syndrome. Subjects with this metabolic condition have defective FMO3 enzyme; and as such, impaired capacity to convert TMA into TMAO. Genome-wide association studies have been recently successful in finding the gene of FMO3 enzyme, which is located in chromosome region 1q23-25. In agreement with this hypothesis, a study by Wranne et al. (Acta Medica Scandinavicia, Vol. CLIII, Fasc VI (1956)) has indicated that the extent of liver damage is accompanied by a reduced capacity of the liver to transform TMA to TMAO. In this study, Wranne et al. had examined the urinary excretion of TMA and TMAO following the administration of TMA to healthy individual and to patients with liver disease. The ratio of TMAO/TMA was markedly reduced in patients with severe liver dysfunction, a finding which suggests that the physiological oxidation of TMA in impaired in patients with liver disease. It remains to be determined, however, whether the FMO3 enzyme activity is decreased in patients with acute AH compared to patients with other forms of liver disease and healthy control.

Another theory may be hypothesized regarding the mechanism behind a TMA level which is remarkably elevated in patients with AH compared to those with other forms of liver disease and healthy individuals. TMA is derived from the degradation of dietary phosphatidylcholine and dietary free choline by the intestinal microflora. Alcohol consumption in patients with alcoholic liver disease induces bacterial overgrowth and increases gut permeability and the translocation of bacteria-derived lipopolysaccharides from the gut to the liver. These may ultimately contribute to the increased levels of TMA in patients with acute AH.

Among patients with acute AH, the levels of exhaled breath TMA moderately correlate with the severity of acute AH as presented by the MELD score. This is driven by the correlation between breath TMA and serum creatinine in patients with AH. Interestingly, there seemed to be no correlation between breath TMA and serum creatinine in a separate cohort of patients with renal insufficiency without liver disease. It is yet to be determined whether TMA has any detrimental effect on the liver cells or just represents a marker of severe liver dysfunction in patients with AH.

Among patients with chronic liver disease, there was no correlation found between the stage of fibrosis on liver biopsy and the level of TMA in the exhaled breath. However, study results were limited by the relatively small number of patients included in the study. In summary, the exhaled breath analysis may provide a non-invasive method for the diagnosis of acute AH and, optionally, also to assess the severity of liver disease in patients with AH. Larger studies should be conducted to validate these findings, and to examine the prognostic values of TMA breath test in patients with acute AH.

Patients Characteristics

In another study, a total of eighty patients were included in the study, of whom forty were admitted with AH in the background of cirrhosis, and forty subjects with AD of liver cirrhosis. Forty-three healthy subjects without liver disease were identified and served as a control group.

Patients with liver disease were older than healthy control (51.4±11.4 vs. 37.9±13.6 years, p<0.001), and predominantly males [43 (53.8%) vs. 14 (32.6%), p=0.025]. The demographic and clinical characteristics of the study population are shown in Table-6.

TABLE 6

Demographic and Clinical Characteristics of the study groups

| Factor | Cirrhosis with Acute De-compensation (N = 40) | Cirrhosis with Alcoholic Hepatitis (N = 40) | p-value |
|---|---|---|---|
| Male | 26 (65.0) | 17 (42.5) | 0.044 |
| Age (years) | 55.8 ± 10.3 | 47.0 ± 11.0 | <0.001 |
| Caucasian | 36 (90.0) | 37 (92.5) | 0.99 |
| ALK (U/L) | 111.0 [90.0, 165.0] | 156.0 [97.0, 212.0] | 0.075 |
| AST (U/L) | 49.5 [37.5, 73.5] | 100.0 [77.0, 142.0] | <0.001 |
| ALT (U/L) | 27.0 [21.0, 36.0] | 47.0 [30.0, 65.0] | <0.001 |
| Bilirubin (mg/dL) | 4.0 [2.0, 8.7] | 14.2 [8.4, 23.3] | <0.001 |
| Albumin (g/dL) | 2.9 ± 0.65 | 3.0 ± 0.61 | 0.43 |
| INR | 1.4 [1.2, 1.8] | 1.6 [1.3, 1.9] | 0.19 |
| Creatinine (mg/dL) | 0.93 [0.77, 1.6] | 0.75 [0.54, 1.6] | 0.029 |
| MELD Score | 19.3 ± 8.0 | 23.5 ± 8.8 | 0.03 |
| Ascites | 27 (67.5) | 22 (56.4) | 0.31 |
| Hepatic Encephalopathy | 26 (65.0) | 27 (67.5) | 0.88 |
| Child's Pugh Score | 10.2 ± 1.9 | 10.1 ± 1.9 | 0.69 |
| Child's Pugh Class | | | |
| B | 14 (35.0) | 16 (40.0) | |
| C | 26 (65.0) | 22 (57.9) | 0.52 |
| Lactulose | 26 (65.0) | 27 (67.5) | 0.81 |
| Rifaximin | 26 (65.0) | 22 (57.9) | 0.36 |

Values presented as Mean ± SD with ANOVA;
Median [P25, P75] with Kruskal-Wallis test, or N (%) with Pearson's chi-square test.
ALK = Alkaline phosphatase,
AST = Asparate amino-transferase,
ALT = alanine amino-transferase,
PT = Prothrombin time,
INR = international normalized ratio,
MELD = Model for end-stage liver disease.

Among patients with AD, 20 had cirrhosis secondary to remote history of alcohol abuse. The other 20 AD patients had liver cirrhosis secondary to the following etiologies [non-alcoholic steatohepatitis (n=8), chronic hepatitis C (n=7), chronic hepatitis B (n=1), alpha-1 antitrypsin deficiency (n=2), primary sclerosing cholangitis (n=1) and cardiac cirrhosis (n=1)].

Among patients with AH, liver biopsy was obtained to confirm the diagnosis in 21 (53%) patients. All patients with AH had liver cirrhosis based on the histological features and/or radiological evidence of cirrhosis in the context of manifestations of portal hypertension (ascites, encephalopathy, variceal bleed or thrombocytopenia). Seventy-two percent of patients with AH had severe disease as defined by MDF score greater than 32, of whom 23% were treated with corticosteroids, 18% with pentoxifylline, and 31% with combination of corticosteroids and pentoxifylline.

At the time of enrollment, the baseline MELD score in the AH patients was 23.5±8.8, compared to 19.3±8.0 in AD patients (p=0.03). This was driven by remarkably higher bilirubin values in patients with AH compared to AD [14.2 (8.4, 23.3) vs. 4.0 (2.0, 8.7) mg/dL, p<0.001].

The Child Pugh scores of patients with AH and AD were closely similar (10.1±1.9 vs. 10.2±1.9, p=0.69), with 16 (40%) AH and 14 (35%) AD subjects classified as class B and 22 (60%) AH and 26 (65%) AD patients as class C Childs-Pugh-Turcotte. Hepatic encephalopathy and ascites were equally present between AH and AD patients (Table-6). Additionally, the uses of lactulose or rifaximin at the time of sampling were not different between the two groups (Table-6).

Breathprints in Patients with Liver Disease

Of the fourteen pre-selected SIM compounds, we identified six exhaled breath compounds that were elevated in patients with liver disease compared to healthy control (Table-7). Those compounds include: 2-propanol, acetaldehyde, acetone, ethanol, pentane, and TMA. There were no differences in the breath levels of benzene, acrylonitrile, carbon disulfide, dimethyl sulfide, isoprene, ammonia, hydrogen sulfide or triethylamine in patients with liver disease compared to healthy control (Table-7).

TABLE 7

Breath Compounds in the healthy control and patients with liver disease - Age and Gender adjusted values

| Dependent | Healthy Control (N = 43) | Liver Patients* (N = 80) | p-value |
|---|---|---|---|
| 2-propanol | 34.0 (27.1, 42.7) | 70.5 (60.6, 82.0) | <0.001 |
| acetaldehyde | 22.8 (18.1, 28.7) | 48.8 (41.9, 56.8) | <0.001 |
| acetone | 77.5 (51.4, 116.8) | 389.5 (297.1, 510.6) | <0.001 |
| acrylonitrile | 0.63 (0.55, 0.72) | 0.74 (0.68, 0.81) | 0.053 |
| benzene | 3.2 (2.3, 4.4) | 2.9 (2.3, 3.6) | 0.63 |
| carbon disulfide | 1.9 (1.5, 2.4) | 2.3 (2.0, 2.7) | 0.18 |
| dimethyl sulfide | 1.3 (1.01, 1.7) | 1.6 (1.4, 1.9) | 0.22 |
| ethanol | 44.8 (33.5, 59.8) | 129.0 (106.5, 156.2) | <0.001 |
| isoprene | 12.8 (9.7, 16.9) | 17.2 (14.3, 20.7) | 0.1 |
| pentane | 9.6 (7.4, 12.3) | 27.1 (23.0, 32.1) | <0.001 |
| ammonia | 62.5 (54.9, 71.1) | 68.0 (62.4, 74.1) | 0.31 |
| hydrogen sulfide | 0.37 (0.26, 0.52) | 0.43 (0.34, 0.53) | 0.49 |
| triethyl amine | 0.70 (0.53, 0.92) | 0.89 (0.74, 1.07) | 0.18 |
| trimethyl amine (TMA) | 4.1 (3.0, 5.6) | 20.7 (16.7, 25.8) | <0.001 |

*Liver patients include patients with cirrhosis and alcoholic hepatitis and those with cirrhosis and acute decompensation.
Values presented as Mean (95% CL) and p-values obtained from Analysis of Covariance (ANCOVA).
The natural logarithm of each compound was modeled as the outcome variable with group, gender and age as the independent variables.

Of the six breath compounds that were higher in patients with liver disease compared to healthy control, there were four breath compounds that stood out in patients with AH. The breath concentrations of acetaldehyde, TMA, acetone and pentane were significantly higher in patients with AH compared to those with AD, while the concentrations of other volatile compounds (2-propanol, acrylonitrile, carbon disulfide, dimethyl sulfide, ethanol, isoprene, ammonia, hydrogen sulfide or triethylamine) in the exhaled breath were not different between patients with AH and those with AD (Table-8).

TABLE 8

Breath Compounds in the patients with liver cirrhosis and alcoholic hepatitis versus those with liver cirrhosis and acute de-compensation - Age and Gender adjusted values

| Dependent | Cirrhosis with Acute De-compensation (N = 40) | Cirrhosis with Alcoholic Hepatitis (N = 40) | p-value |
|---|---|---|---|
| 2-propanol | 72.5 (59.8, 87.8) | 72.0 (59.6, 87.0) | 0.96 |
| acetaldehyde | 41.2 (33.3, 51.0) | 57.0 (46.2, 70.4) | 0.043 |
| acetone | 188.5 (133.9, 265.6) | 703.4 (501.9, 985.7) | <0.001 |
| acrylonitrile | 0.77 (0.68, 0.89) | 0.74 (0.65, 0.85) | 0.69 |
| benzene | 3.3 (2.5, 4.5) | 2.8 (2.1, 3.7) | 0.38 |
| carbon disulfide | 2.3 (1.8, 3.0) | 2.4 (1.8, 3.1) | 0.81 |
| dimethyl sulfide | 1.7 (1.3, 2.3) | 1.7 (1.3, 2.2) | 0.92 |
| ethanol | 159.5 (117.5, 216.3) | 115.3 (85.4, 155.7) | 0.15 |
| isoprene | 18.2 (14.3, 23.3) | 17.6 (13.8, 22.4) | 0.84 |
| pentane | 17.5 (13.7, 22.4) | 37.7 (29.6, 48.0) | <0.001 |
| ammonia | 71.4 (63.0, 81.1) | 68.4 (60.4, 77.5) | 0.64 |
| hydrogen sulfide | 0.39 (0.27, 0.57) | 0.48 (0.33, 0.70) | 0.48 |
| triethyl amine | 0.88 (0.64, 1.2) | 0.90 (0.66, 1.2) | 0.95 |
| trimethyl amine (TMA) | 10.2 (7.7, 13.5) | 34.2 (26.4, 44.4) | <0.001 |

Values presented as Mean (95% CL) and p-values obtained from Analysis of Covariance (ANCOVA).
The natural logarithm of each compound was modeled as the outcome variable with group, gender and age as the independent variables.

Breath-Biomarkers in AH and TAP Score

After adjusting for age and gender, the concentrations of acetaldehyde, TMA, acetone and pentane in the breath were significantly higher in patients with liver cirrhosis and AH compared to those with liver cirrhosis and AD, and compared to healthy volunteers (Table-8). The association between TMA, acetone and pentane in the exhaled breath and AH remained significant after accounting for MELD score (all p<0.001). Furthermore, the significance of the breath's acetone, pentane and TMA in patients with AH remained the same after excluding patients with clinical diagnosis but no histological confirmation of AH (all p<0.001).

Figure 4:
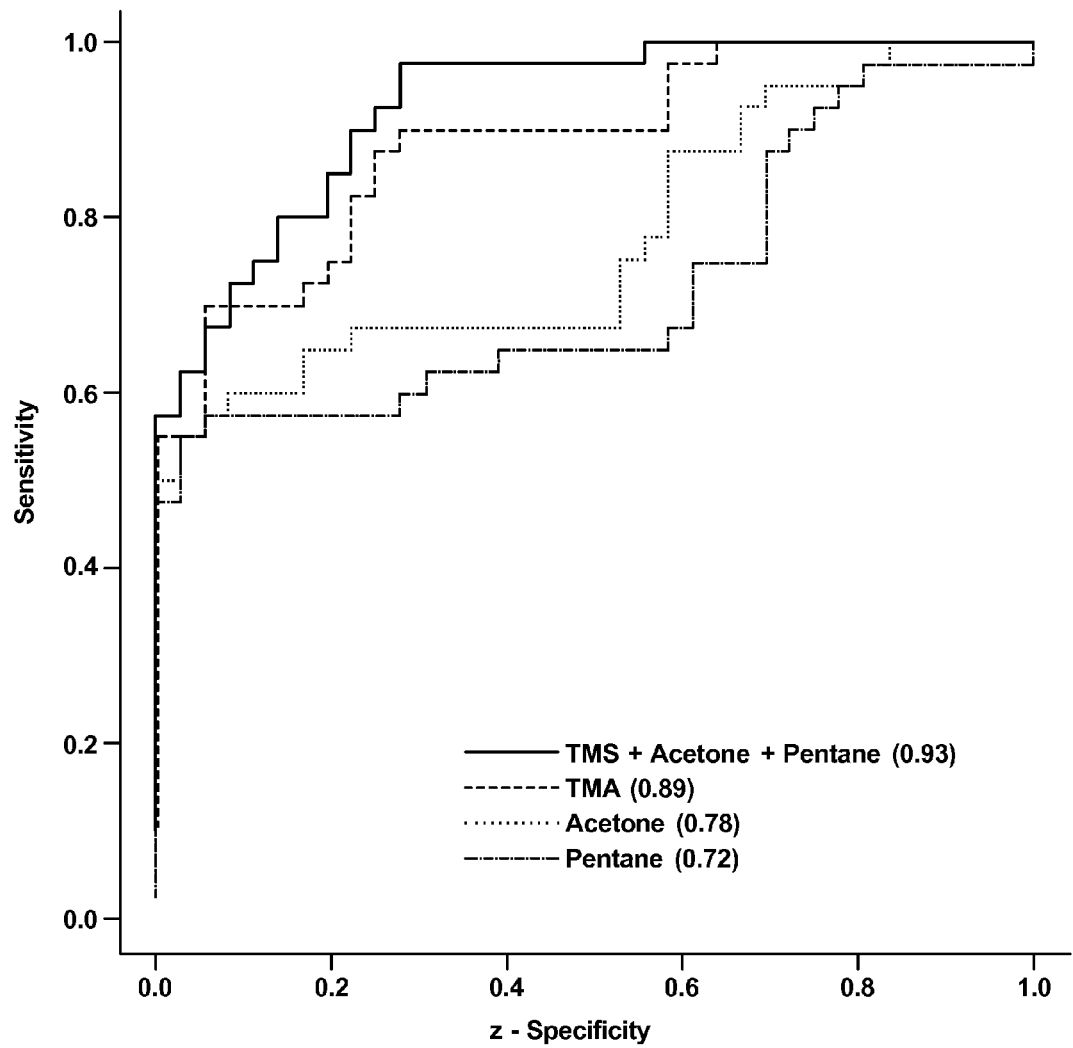
FIG. 4 is a graph depicting Trimethylamine (TMA) levels in the exhaled breath of patients with various forms of liver disease, according to an embodiment of the present invention.

FIG. 4 presents the results of the ROC analysis. A cutoff value of breath TMA of 14 ppb provided 90% sensitivity and 72% specificity for the diagnosis of AH [AUC 95% CI: 0.887 (0.815, 0.959)]. Breath's acetone and pentane were less sensitive but more specific for the diagnosis of AH. A breath acetone value of 489 ppb was 60% sensitive and 92% specific [AUC 95% CI: 0.778 (0.673, 0.883)]; and a breath pentane value of 30 ppb was 57% sensitive and 95% specific in the diagnosis of AH. A combination of acetone, pentane and TMA levels in the breath was found to provide excellent prediction accuracy for the diagnosis of AH (AUC=0.93).

A logistic regression (lr) function combining the three breath variables; TMA, Acetone, and Pentane for the diagnosis of AH was [lr=−4.39+(0.46×TMA)−(0.0032×Acetone)−(0.091×Pentane)]. The logistic function (lr) value was then converted into a probability distribution with a value between 0 to 100 and called "TAP score" by the following formula: TAP score=100×[exp(lr)/[1+exp(lr)]. A TAP score of 28 provided 97% sensitivity and 72% specificity for the diagnosis of AH; and a TAP score of 51 was 80% sensitive and 86% specific for the diagnosis of AH. The predictive value of the breath's acetaldehyde for the diagnosis of AH was not strong (AUC=0.60 (95% CI: 0.48, 0.73); hence it was not included in the TAP model.

Another logistic regression (lr) function combining two breath variables, TAP for the diagnosis of AH was [lr=−

3.71+[0.34×TMA]−[0.087×pentane]. The logistic function (lr) was then converted into a robablility distribution with a value between 0 and 100 and called "TAP score" by the following formula: TAP score=100×(exp[lr]/1+exp[lr]). A TAP score of 36 provided 90% sensitivity and 80% specificity for the diagnosis of AH. A TAP score of 67 was 70% sensitive and 94% specific for the diagnosis of AH.

Breathprint and the Severity of AH

There was a moderate correlation between the concentrations of TMA in the exhaled breath and the severity of liver disease in patients with AH as presented by MELD score [rho (95% CI); 0.38 (0.07, 0.69), p=0.018]. This is largely driven by the association between breath TMA and serum creatinine [rho (95% CI); 0.36 (0.05, 0.67), p=0.026]. There was no correlation between the concentrations of breath TMA and either serum bilirubin [rho (95% CI); 0.28 (−0.03, 0.60), p=0.079] or INR [rho (95% CI); 0.23 (−0.09, 0.56), p=0.15]. Therefore, the association between TMA levels in the breath and MDF score [rho (95% CI); 0.30 (−0.02, 0.62), p=0.062], and CPS [rho (95% CI); 0.1 7 (−0.16, 0.50), p=0.31] did not reach statistically significant values (Table-9).

TABLE 9

Breath compounds and the severity of liver disease in alcoholic hepatitis.

| Factor | MELD Score | | Child's Pugh Score | | Maddrey's Function | |
|---|---|---|---|---|---|---|
| | rho (95% CI) | p-value | rho (95% CI) | p-value | rho (95% CI) | p-value |
| 2-propanol | −0.04 (−0.37, 0.29) | 0.81 | 0.01 (−0.32, 0.35) | 0.94 | −0.06 (−0.39, 0.27) | 0.73 |
| acetaldehyde | 0.25 (−0.07, 0.57) | 0.13 | 0.10 (−0.24, 0.43) | 0.57 | 0.19 (−0.14, 0.52) | 0.25 |
| acetone | 0.29 (−0.03, 0.61) | 0.076 | 0.06 (−0.28, 0.39) | 0.73 | 0.23 (−0.10, 0.55) | 0.17 |
| acrylonitrile | −0.27 (−0.59, 0.05) | 0.092 | −0.12 (−0.46, 0.22) | 0.47 | −0.28 (−0.60, 0.04) | 0.089 |
| benzene | −0.00 (−0.34, 0.33) | 0.98 | 0.02 (−0.32, 0.36) | 0.89 | −0.05 (−0.39, 0.28) | 0.74 |
| carbon disulfide | 0.13 (−0.20, 0.46) | 0.43 | 0.05 (−0.29, 0.39) | 0.77 | 0.05 (−0.29, 0.38) | 0.78 |
| dimethyl sulfide | −0.10 (−0.43, 0.24) | 0.56 | −0.04 (−0.37, 0.30) | 0.83 | −0.03 (−0.36, 0.31) | 0.87 |
| ethanol | 0.18 (−0.15, 0.51) | 0.27 | 0.14 (−0.19, 0.48) | 0.4 | 0.18 (−0.15, 0.51) | 0.27 |
| isoprene | 0.13 (−0.20, 0.46) | 0.42 | 0.09 (−0.25, 0.42) | 0.6 | 0.12 (−0.21, 0.45) | 0.46 |
| pentane | 0.30 (−0.01, 0.62) | 0.06 | 0.12 (−0.21, 0.46) | 0.47 | 0.22 (−0.11, 0.54) | 0.19 |
| ammonia | 0.23 (−0.10, 0.55) | 0.17 | 0.11 (−0.23, 0.44) | 0.52 | 0.28 (−0.04, 0.60) | 0.09 |
| hydrogen sulfide | 0.15 (−0.18, 0.48) | 0.35 | −0.02 (−0.36, 0.31) | 0.89 | 0.12 (−0.21, 0.45) | 0.48 |
| triethylamine | −0.13 (−0.46, 0.20) | 0.43 | 0.01 (−0.33, 0.35) | 0.95 | −0.06 (−0.39, 0.27) | 0.72 |
| Trimethylamine (TMA) | 0.38 (0.07, 0.69) | 0.018 | 0.17 (−0.16, 0.50) | 0.31 | 0.30 (−0.02, 0.62) | 0.062 |

MELD = Model for end-stage liver disease

Similarly, the associations between the breath's pentane and acetone and the MELD score in AH subjects were not statistically significant [pentane: 0.30 (−0.01, 0.62), p=0.06 and acetone: 0.29 (−0.03, 0.61), p=0.076]. There was no significant correlation between the concentrations of other volatile breath compounds and the severity of liver disease in patients with AH as presented by MELD score, MDF scores or CPS (Table-9).

Breathprint and the Transplant-Free Survival in AH

Subjects with AH were followed over 7.3±7.0 months (range 0.1 to 22.4 months) during which 11 (27%) died and 1/40 (2%) received liver transplantation. Table-10 presents the univariable hazard ratios assessing the associations between the concentration of volatile breath compounds and transplant-free survival.

TABLE 10

Breath compounds and transplant-free survival in patients with alcoholic hepatitis (AH)

| Factor (10 unit increase unless otherwise specified) | AH (n = 40) | | AH treated with steroids (n = 21) | |
|---|---|---|---|---|
| | Hazard Ratio (95% CI) | p-value | Hazard Ratio (95% CI) | p-value |
| 2-propanol | 0.92 (0.77, 1.10) | 0.37 | 0.84 (0.64, 1.1) | 0.22 |
| acetaldehyde | 1.00 (0.93, 1.07) | 0.99 | 0.93 (0.78, 1.10) | 0.38 |
| acetone (25 unit increase) | 1.00 (0.95, 1.06) | 0.87 | 0.94 (0.81, 1.09) | 0.39 |
| acrylonitrile (1 unit increase) | 0.56 (0.08, 4.0) | 0.56 | 0.62 (0.02, 16.4) | 0.78 |
| benzene | 2.0 (0.97, 4.1) | 0.061 | 0.84 (0.16, 4.4) | 0.84 |
| carbon disulfide | 1.02 (0.70, 1.5) | 0.91 | 0.11 (0.00, 17.7) | 0.39 |
| dimethyl sulfide | 0.81 (0.38, 1.7) | 0.58 | 0.10 (0.00, 424.1) | 0.59 |
| ethanol | 1.02 (1.01, 1.04) | 0.005 | 1.03 (1.01, 1.05) | 0.014 |

TABLE 10-continued

Breath compounds and transplant-free survival in patients with alcoholic hepatitis (AH)

| Factor (10 unit increase unless otherwise specified) | AH (n = 40) | | AH treated with steroids (n = 21) | |
|---|---|---|---|---|
| | Hazard Ratio (95% CI) | p-value | Hazard Ratio (95% CI) | p-value |
| isoprene | 1.3 (1.04, 1.6) | 0.022 | 1.3 (0.86, 1.9) | 0.22 |
| pentane | 1.02 (0.97, 1.07) | 0.54 | 0.95 (0.82, 1.09) | 0.44 |
| ammonia | 1.08 (0.93, 1.3) | 0.32 | 0.96 (0.71, 1.3) | 0.79 |
| hydrogen sulfide (1 unit increase) | 1.00 (1.00, 1.01) | 0.49 | 0.01 (0.00, 16.5) | 0.23 |
| triethyl amine (1 unit increase) | 0.67 (0.11, 4.1) | 0.67 | 0.34 (0.03, 3.9) | 0.39 |
| trimethyl amine (TMA) | 1.00 (0.95, 1.06) | 0.86 | 0.95 (0.83, 1.08) | 0.43 |

Two breath compounds (isoprene and ethanol) were associated with transplant-free survival in patients with AH. For every 10 ppb increase in the breath levels of isoprene, the mortality rate in patients with AH increased by 20% (p=0.044). Among subjects with AH who were treated with corticosteroids (53%), breath ethanol predicted poor survival outcome. For every 10 ppb increase in the breath concentrations of ethanol, the mortality rate increased by 3% (p=0.014).

The levels of other volatile breath compounds including TMA, acetone and pentane were not associated with survival rates in patients with AH.

The complete disclosure of all patents, patent applications, and publications, and electronically available material cited herein are incorporated by reference. The foregoing detailed description and examples have been given for clarity of understanding only. No unnecessary limitations are to be understood therefrom. Although the invention has been described with reference to several specific embodiments, the invention is not limited to the exact details shown and described, for variations obvious to one skilled in the art will be included. The description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

Having described the invention, we claim:

1. A method for assessing a subject as having alcoholic hepatitis (AH) comprising:
   receiving an exhaled breath sample from a subject;
   determining the level of trimethylamine (TMA) and the level of pentane in the exhaled breath sample obtained from the subject using an analytical device;
   determining a TAP score based on the concentration of trimethylamine and the concentration of pentane in the exhaled breath; and
   diagnosing the subject as having alcoholic hepatitis based on the TAP score.

2. The method of claim 1, wherein the TAP score is determined according to the formula:

$TAP$ score=$100 \times (\exp[lr]/1+\exp[lr])$, wherein ($lr$=−3.71+[0.34×trimethylamine]−[0.087×pentane]).

3. The method of claim 1, wherein the subject is diagnosed as having alcoholic hepatitis when the TAP score is at least about 34.

4. The method of claim 1, wherein the TAP score ranges from about 36 to about 67.

5. The method of claim 1, wherein the TAP score is at least about 67.

6. The method of claim 1, further comprising the step of rinsing the mouth of the subject to remove volatile compounds before obtaining an exhaled breath sample from the subject.

7. The method of claim 6, wherein the mouth of the subject is rinsed before obtaining an exhaled breath sample from the subject.

8. The method of claim 1, wherein the analytic device is a sensor.

9. The method of claim 1, wherein the analytical device is a mass spectrometer or a differential mobility spectroscopy (DMS) sensor.

10. The method of claim 1, wherein the analytical device is a selected-ion flow-tube mass spectrometry (SIFT-MS).

11. The method of claim 1, wherein the subject is a healthy subject.

12. The method of claim 1, wherein the subject has been diagnosed as having liver disease.

13. The method of claim 1, wherein the subject has been diagnosed as having alcoholism.

14. The method of claim 1, wherein the exhaled breath sample is stored for less than about 4 hours before determining the TAP score.

15. The method of claim 1, wherein the analytical device comprises a gas collection component for receiving a biological sample which is a breath sample;
   and a sensor capable of detecting ppb level of trimethylamine and ppb level of pentane collected in the gas collection component.

16. The method of claim 15, wherein the exhaled breath of the subject is filtered by the gas collection component.

17. The method of claim 1, wherein the subject is a non-smoker.

18. The method of claim 1, wherein the method further comprises providing therapeutic intervention to a subject identified as having alcoholic hepatitis (AH).

19. A method for assessing a subject as having acute alcoholic hepatitis (AH) comprising:
   receiving an exhaled breath sample from a subject;
   determining the level of trimethylamine (TMA), the level of acetone, and the level of pentane in the exhaled breath sample obtained from the subject using an analytical device;
   determining a TAP score based on the concentration of trimethylamine, the concentration of acetone, and the concentration of pentane in the exhaled breath; and diagnosing the subject as having alcoholic hepatitis based on the TAP score.

20. The method of claim 19, wherein the TAP score is determined according to the formula:

$$TAP\ score = 100 \times (\exp[lr]/1+\exp[lr])\ wherein$$

$$(lr = -4.39 + [0.46 \times trimethylamine] - [0.0032 \times acetone] - (0.091 \times pentane).$$

21. The method of claim 19, wherein the subject is diagnosed as having alcoholic hepatitis if the TAP score ranges from about 25 to about 55.

22. The method of claim 19, wherein the subject is diagnosed as having alcoholic hepatitis if the TAP score is at least about 28.

23. A method of identifying a subject having acute alcoholic hepatitis (AH), comprising:
    receiving an exhaled breath sample from a subject;
    determining the level of trimethylamine (TMA) in the exhaled breath sample obtained from the subject using an analytic device; and
    diagnosing a subject as having alcoholic hepatitis if the exhaled breath sample contains a level of trimethylamine that ranges from about 14 ppb to about 40 ppb.

24. A method of identifying a subject having acute alcoholic hepatitis (AH), comprising:
    receiving an exhaled breath sample from a subject;
    determining the level of trimethylamine (TMA) in the exhaled breath sample obtained from the subject using an analytic device; and
    diagnosing a subject as having alcoholic hepatitis if the exhaled breath sample contains a level of trimethylamine that is at least about 40 ppb.

25. A method of identifying a subject having acute alcoholic hepatitis (AH), comprising:
    receiving an exhaled breath sample from a subject;
    determining the level of pentane in the exhaled breath sample obtained from the subject using an analytic device; and
    diagnosing a subject as having alcoholic hepatitis if the exhaled breath sample contains a level of pentane that ranges from about 30 ppb to about 50 ppb.

26. A method of identifying a subject having acute alcoholic hepatitis (AH), comprising:
    receiving an exhaled breath sample from a subject;
    determining the level of pentane in the exhaled breath sample obtained from the subject using an analytic device; and
    diagnosing a subject as having alcoholic hepatitis if the exhaled breath sample contains a level of pentane that is at least about 50 ppb.

27. A method of identifying a subject having acute alcoholic hepatitis (AH), comprising:
    receiving an exhaled breath sample from a subject;
    determining the level of acetone in the exhaled breath sample obtained from the subject using an analytic device;
    diagnosing a subject as having alcoholic hepatitis if the exhaled breath sample contains a level of acetone that ranges from about 450 ppb to about 550 ppb.

28. A method of identifying a subject having acute alcoholic hepatitis (AH), comprising:
    receiving an exhaled breath sample from a subject;
    determining the level of acetone in the exhaled breath sample obtained from the subject using an analytic device;
    diagnosing a subject as having alcoholic hepatitis if the exhaled breath sample contains a level of acetone that is at least about 550 ppb.

* * * * *